(12) United States Patent
Hongo et al.

(10) Patent No.: US 9,726,636 B2
(45) Date of Patent: Aug. 8, 2017

(54) SINGLE PARTICLE ANALYZER AND SINGLE PARTICLE ANALYSIS METHOD

(71) Applicants: KABUSHIKI KAISHA TOSHIBA, Minato-ku (JP); OSAKA UNIVERSITY, Suita-shi (JP)

(72) Inventors: Sadato Hongo, Yokohama (JP); Tomoji Kawai, Minoh (JP); Makusu Tsutsui, Toyonaka (JP); Masateru Taniguchi, Ibaraki (JP); Soh Ryuzaki, Minoh (JP)

(73) Assignees: KABUSHIKI KAISHA TOSHIBA, Minato-ku (JP); OSAKA UNIVERSITY, Suita-shi (JP)

(*) Notice: Subject to any disclaimer, the term of this patent is extended or adjusted under 35 U.S.C. 154(b) by 390 days.

(21) Appl. No.: 14/484,305

(22) Filed: Sep. 12, 2014

(65) Prior Publication Data
US 2014/0374255 A1 Dec. 25, 2014

Related U.S. Application Data

(63) Continuation of application No. PCT/JP2013/056690, filed on Mar. 11, 2013.

(51) Int. Cl.
*G01N 27/447* (2006.01)
*G01N 15/12* (2006.01)
(Continued)

(52) U.S. Cl.
CPC ....... *G01N 27/44756* (2013.01); *G01N 15/12* (2013.01); *G01N 15/1218* (2013.01);
(Continued)

(58) Field of Classification Search
CPC .......... G01N 33/48721; G01N 15/12–15/1218
See application file for complete search history.

(56) References Cited

U.S. PATENT DOCUMENTS

| 2,656,508 A | 10/1953 | Coulter |
| 5,719,666 A * | 2/1998 | Fukuda .............. G01N 15/1456 356/317 |
| 2009/0136958 A1 | 5/2009 | Gershow et al. |

FOREIGN PATENT DOCUMENTS

JP 2011-501806 A 1/2011

OTHER PUBLICATIONS

International Preliminary Report on Patentability and Written Opinion issued Oct. 9, 2014 in PCT/JP2013/056690 (with English translation).
(Continued)

*Primary Examiner* — Alexander Noguerola
(74) *Attorney, Agent, or Firm* — Oblon, McClelland, Maier & Neustadt, L.L.P.

(57) ABSTRACT

According to one embodiment, provided is a single particle analyzing device including a measuring vessel, first and second chambers in the vessel defined by an insulating membrane, a pore opening in the membrane to connect the chambers, and first and second electrodes in the chambers. Electric current flows between the electrodes through the pore. Electrical characteristics are measured during migration of the target from the first chamber to the second chamber to measure the size and shape of the target. (a) $t<a<d\leq 100a$ or (b) $s<L$, $s<d\leq 100s$, $t<L$ and $t<d$, wherein a, L and s are the diameter, length and width of the target, d is the diameter of the pore, and t is the thickness of the membrane in the proximity to the pore.

15 Claims, 13 Drawing Sheets

(51) Int. Cl.
G01N 33/487 (2006.01)
G01N 15/10 (2006.01)

(52) U.S. Cl.
CPC ............... *G01N 33/48721* (2013.01); *G01N 2015/1062* (2013.01); *G01N 2015/1087* (2013.01); *G01N 2015/1093* (2013.01)

(56) References Cited

OTHER PUBLICATIONS

International Search Report issued on May 21, 2013 for PCT/JP2013/056690 filed on Mar. 11, 2013 with English Translation.
International Written Opinion mailed on May 21, 2013 for PCT/JP2013/056690 filed on Mar. 11, 2013.
Taniguchi, Masateru et al., "Single-Molecule Identification Using Gating Nanopores", The Institute of Electrical Engineers of Japan, Bio Micro System Symposium (BMS-10-004), 2010, pp. 1-5 with English Abstract.
Tsutsui, Makusu et al., "Single-Nanoparticle Detection Using a Low-Aspect-Ratio Pore", ACS Nano, vol. 6, No. 4, 2012, pp. 3499-3505.
Garaj, S. et al., "Graphene as a subnanometre trans-electrode membrane", Nature, vol. 467, 2010, 5 pgs.
Merchant, Christopher A. et al., "DNA Translocation through Graphene Nanopores", Nano Letters, vol. 10, 2010, pp. 2915-2921.

* cited by examiner

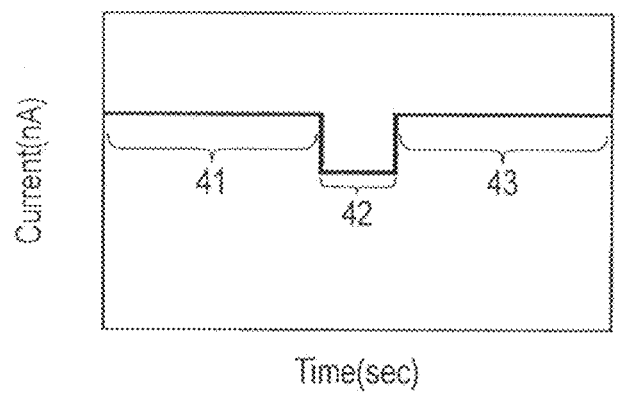
F I G. 4
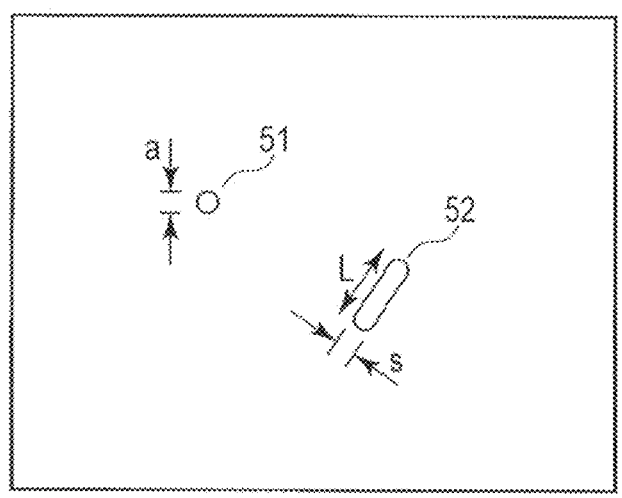
F I G. 5

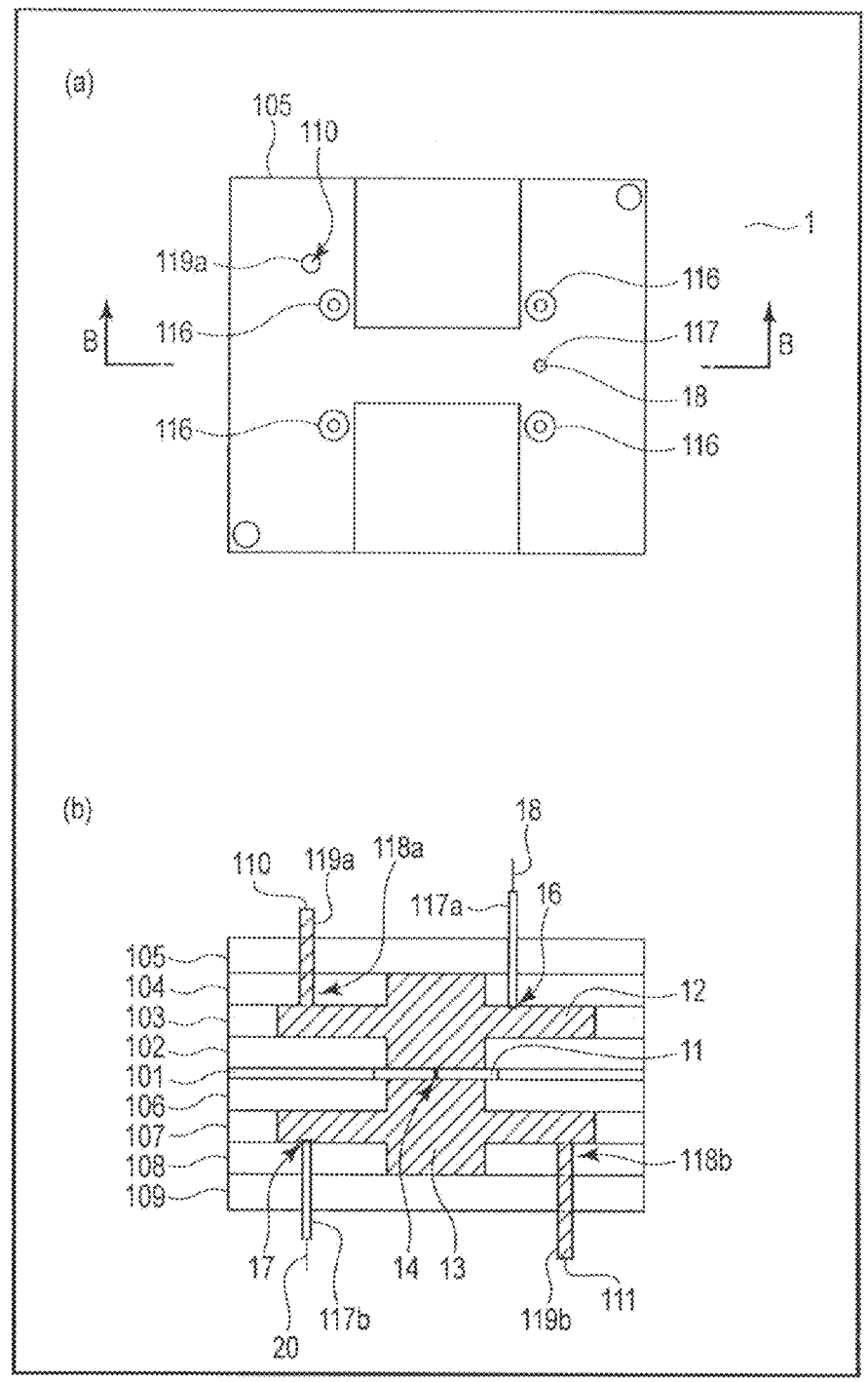
F I G. 10

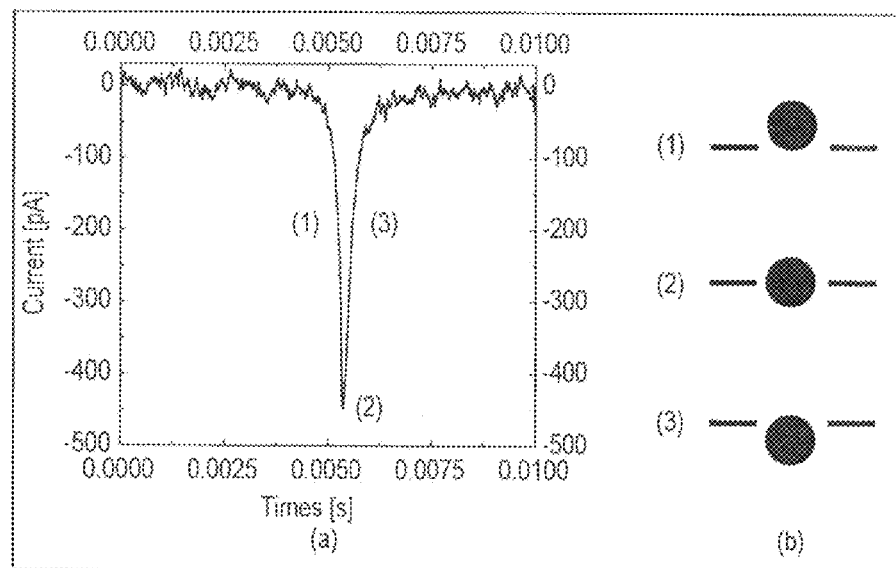
F I G. 15
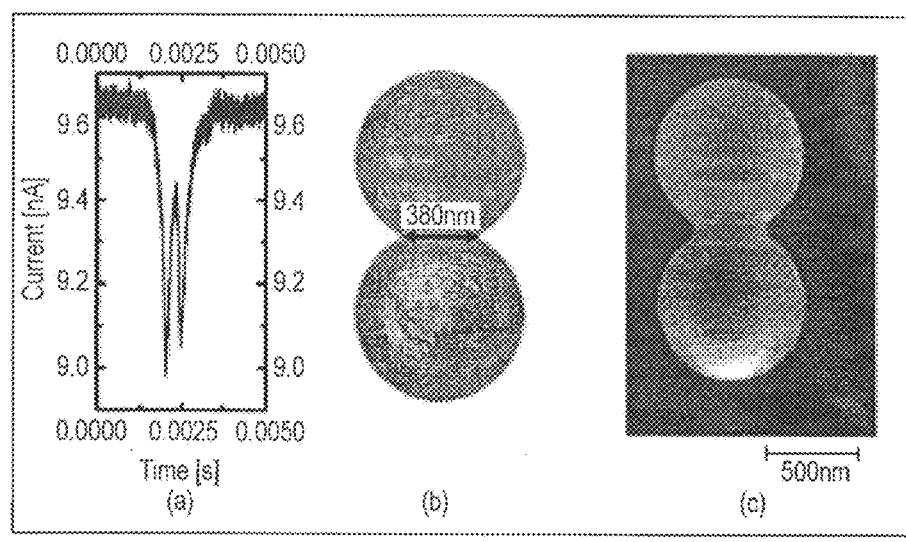
F I G. 16

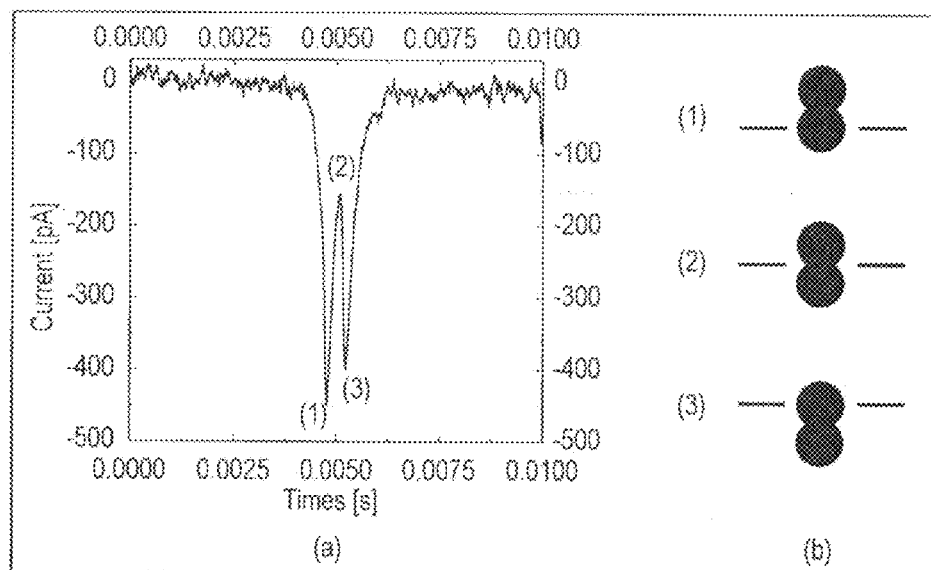
F I G. 17
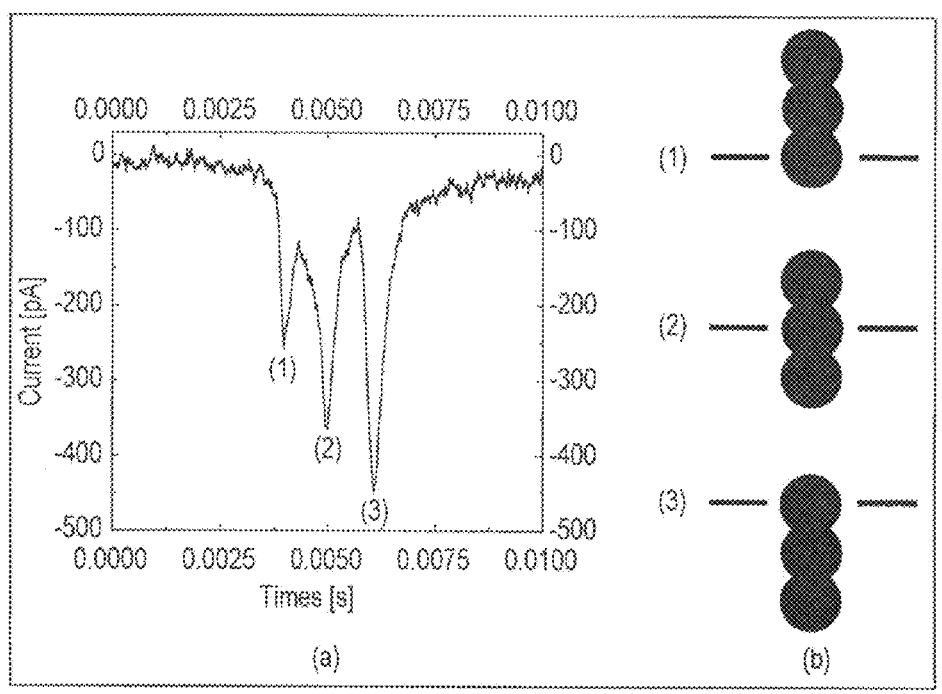
F I G. 18

SINGLE PARTICLE ANALYZER AND SINGLE PARTICLE ANALYSIS METHOD

CROSS REFERENCE TO RELATED APPLICATIONS

This application is a Continuation Application of PCT Application No. PCT/JP2013/056690, filed Mar. 11, 2013 and based upon and claiming the benefit of priority from International Application No. PCT/JP2012/056372, filed Mar. 13, 2012, the entire contents of all of which are incorporated herein by reference.

FIELD

Embodiments described herein relate generally to a single particle analyzing device and a single particle analysis method.

BACKGROUND

To identify viruses and bacteria, there are well-known methods such as a PCR method which identifies genes, a DNA chip utilizing method, and an ELISA method which utilizes an antigen-antibody reaction. In addition to these methods, there is an attempt to detect viruses and bacteria by recognizing the size of each particle in a specimen.

BRIEF DESCRIPTION OF THE DRAWINGS

FIG. 4 is a graph showing an example of a signal detected in the embodiments.

FIG. 5 is a schematic view showing examples of targets.

FIG. 10 includes a plane view and a cross-sectional view showing the embodiments.

FIG. 15 is a graph showing an ion current change measured during pass of a monomeric bead through a 1 µm pore.

FIG. 16 includes: (a) a graph showing ion current change; (b) an image showing a shape of a measurement target calculated from the ion current change; and (c) an electron microscopic photo image of the measurement target.

FIG. 17 is a graph showing an ion current change measured during transfer of a dimeric bead from the first chamber to the second chamber and pass of the bead through a 1 µm pore.

FIG. 18 is a graph showing an ion current change measured during transfer of a trimeric bead from the first chamber to the second chamber and pass of the bead through a 1 µm pore.

DETAILED DESCRIPTION

According to one embodiment, provided is a single particle analyzing device including a measuring vessel, a first chamber and a second chamber in the measuring vessel defined by an insulating membrane, a pore opening in the membrane to connect the first chamber to the second chamber, and a first electrode in the first chamber and a second electrode in the second chamber. Electric current flows between the first and second electrodes through the pore in the membrane. Electrical characteristics are measured during trans location of the target from the first chamber transfers to the second chamber through the pore to derive the shape of the target. Therein, (a) $t<a<d\leq100a$, wherein a is the diameter of the target, d is the diameter of the pore, and t is the thickness of the membrane in the proximity to the pore. Or (b) $s<L$, $s<d\leq100s$, $t<L$, and $t<d$, wherein L is the length of the target, s is the width thereof, d is the diameter of the pore, and t is the thickness of the membrane in the proximity to the pore.

Provided is a single particle analyzing device and a single particle analysis method which can identify the difference in size and shape of particles with greater accuracy.

Various Embodiments will be described hereinafter with reference to the accompanying drawings.

(1) Device Structure

Figure 1:
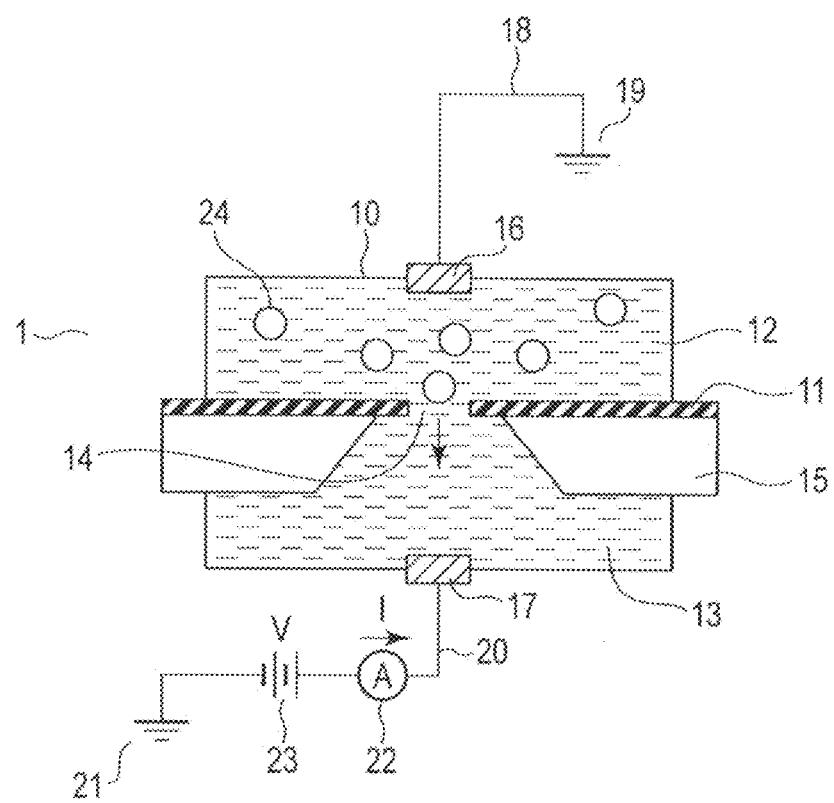
FIG. 1 is a schematic view showing a cross-sectional structure of embodiments.

FIG. 1 is a cross-sectional view showing an example of the single particle analyzing device of the first embodiment. As shown, the single particle analyzing device comprises a measuring vessel 10. The measuring vessel 10 is divided into a first chamber 12 and a second chamber 13 by an insulating membrane 11. A pore 14 passes through a membrane 11 to connect a first chamber 12 to a second chamber 13. The membrane 11 is supported by substrate 15 which has a sufficient thickness and detours around the periphery of the pore 14. The electrodes 16 and 17 are provided with the walls of the measuring vessel 10. The electrode 16 is partly exposed to the first chamber 12. The electrode 17 is partly exposed to the second chamber 13. The electrode 16 is connected to ground 19 through the lead 18. The electrode 17 is connected to earth 21 through the lead 20. The ammeter 22 and power source 23 are provided with lead 20. Note that, the analyzing device shown in FIG. 1 should preferably include a noise removal circuit, a voltage stabilization circuit, and the like in addition to the above.

Figure 2:
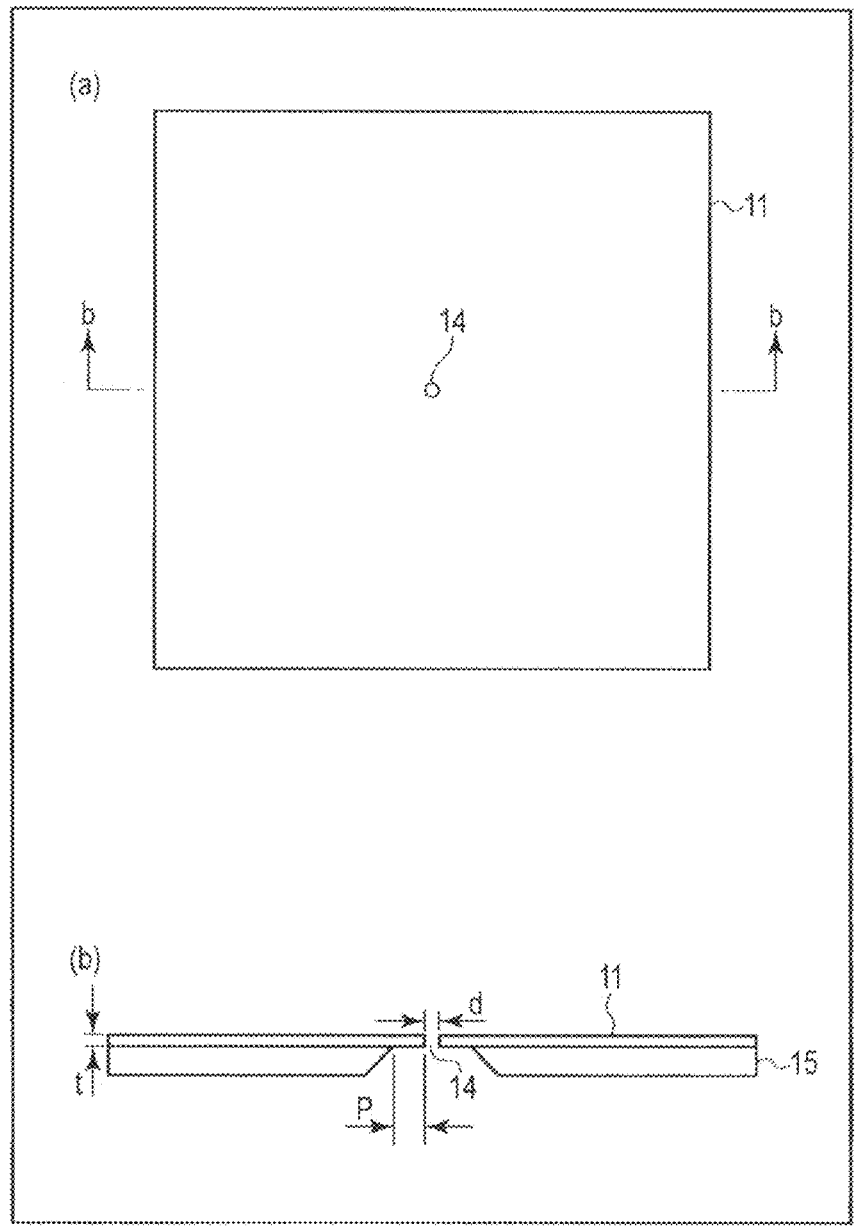
FIG. 2 includes a plane view and a cross-sectional view showing an embodiment of a membrane.

FIG. 2(a) is a plane view showing the membrane 11 being viewed from the first chamber 12 side. The membrane 11 has pore 14 whose opening is circular. FIG. 2(b) is a cross-sectional view of the membrane 11 taken along line b-b. If the diameter of the opening part of pore 14 is given d and the thickness of the membrane 11 is given t, they satisfy:

$t<d$.

The substrate 15 supports the membrane 11 at its entire area except for the proximity of pore 14. That is, the substrate 15 is arranged such that, while a measurement target is passing through the pore 14, only the membrane 11 which defines the pore 14 has an effect on the electric resistance of the measurement target. Thus, the substrate 15 has no effect on the electric resistance of the measurement target while it is passing through the inside of pore 14, and the substrate 15 can be disregarded in the calculation of the electric resistance of the measurement target. The proximity of pore 14 on the membrane 11 is an area ranging from the edge of membrane 11 defining the pore 14 to the substrate 15, and is denoted as symbol p in FIG. 2(b). The proximity of pore 14 ranges concentrically around the pore 14. Preferably, a relationship between the proximity of pore 14 and diameter d of the opening part should satisfy:

P≥d, and more preferably, should satisfy:

p≥0.5d.

The measuring vessel 10 may be entirely formed of an electrically and chemically inactive material which is known publically, or only the inside of first chamber 12, the inside of second chamber 13, a part contacting the first electrode 16, and a part contacting the second electrode may be formed of such a material. For example, glass, sapphire, ceramics, resin, rubber, elastomer, $SiO_2$, SiN, $Al_2O_3$, and the like are adoptable.

The membrane 11 may be formed of an electrically and chemically inactive insulating material such as glass, sapphire, ceramics, resin, rubber, elastomer, $SiO_2$, SiN, and $Al_2O_3$.

The first and second electrodes may be formed of any publically-known electrode material such as Ag/AgCl, Pt, and Au. Preferably, Ag/AgCl electrode should be used.

The volume of the first chamber and the volume of the second chamber may either be the same or different.

The volume of the first chamber may range from 1 zL to 1 mL, and preferably from 1 fL to 1 μL. The volume of the second chamber may range from 1 zL to 1 mL, and preferably from 1 fL to 1 μL. The volume of the first and second chambers can be changed depending on the size of the pore. For example, if diameter d of the pore is in an nm order, that is, 1 nm ≤d<10 nm, the volume of each of the first and second chambers may range from 1 zl to 1 mL or from 1 zL to 10 mL. If diameter d of the pore is in a mm order, that is, 1 mm≤d<10 mm, the volume of each of the first and second chambers may range from 1 μL to 1 mL or 1 μL to 1 L.

The diameter of pore 14 and the thickness of membrane 11 in the proximity to pore 14 may be determined based on the size of the target particle. The details are described below.

(2) Method of Analysis

Using the embodiment shown in FIG. 1, how to measure the size and shape of a particle is now described.

The first chamber 12 and the second chamber 13 are filled with liquid. Here, the pore 14 makes a liquid junction between the first chamber 12 and the second chamber 13. The first chamber 12 contains particles 24 which are the targets. The first electrode 16 and the second electrode 17 are immersed in the liquid charged in the first chamber 12 and the second chamber 13, respectively.

The liquid in the first and second chambers should be a liquid which can conduct electricity between first electrode 16 and second electrode 17. The liquid which can conduct electric current may be an electrolyte solution such as a KCl solution, or a buffer solution such as TE buffer solution and PBS buffer solution.

While the first chamber 12 and second chamber 13 are filled with the solution, the voltage is applied between the first electrode 16 and second electrode 17 by the power source 23. The electric current is measured by the ammeter 22. The particles 24 in the first chamber pass to the second chamber through the pore 14 by diffusion. When one of the particles 24 passes through the pore 14, the current measured by the ammeter 22 decreases depending on the size and shape of this particle 24.

FIG. 4 shows an example of how the current changes as a signal detected in the measurement. The vertical axis is the electric current and the horizontal axis is the measurement time. If there is no particle passing through the pore 14, the electric current measured between the first and second electrodes connected by the pore 14 is constant (41). This current is a base value. If there is one of the particles 24 passing through the pore 14, the electric current decreases depending on the size and shape of this passing particle (42). After the particle passes by the pore 14, the electric current returns to the level measured at the time before the particle enters the pore 14 (43).

The above phenomenon can be explained as follows. When the particle 24 passes through the pore 14 which is an electric current path, it removes electric conductive substances such as ions from the pore 14. This causes the current resistance increase and thus, the current decreases. After the particle 24 passed down through the pore 14, the electric current returns to its original level. One particle passes through, one lowering current signal is measured. By counting the number of lowering current signals, the total number of particles which have passed through the pore 14 can be calculated. Here, the amount of ions to be removed from the pore 14 by the particle 24 varies depending on the size and shape of the particle 24.

In the above example, the particles 24 transfer from the first chamber to the second chamber by the diffusion. However, the transfer is caused not only by the diffusion. For example, the particle transfer may be promoted by electrophoresis or liquid flow working to transfer the particles from the first chamber to the second chamber. When electrophoresis is used to promote the transfer, the electrophoresis may be caused by the electricity between first electrode 16 and second electrode 17. Otherwise, the electrophoresis may be caused by an electrode other than the first electrode 16 and second electrode 17. For example, if the particles 24 are negatively charged, the voltage of second electrode 17 is set to positive generating the electrophoresis from the first chamber to the second chamber. When liquid flow is used to promote the transfer of the particles 24 from the first chamber to the second chamber, the liquid flow may be performed as follows. Firstly, a first opening port to which a liquid is charged is provided with a wall surface of the measuring vessel on the first chamber side. Secondly, a second opening port from which the liquid is discharged is provided with a wall surface of the measuring vessel on the second chamber side. The liquid flowing in the first opening port and/or flowing out of the second opening port promotes the transfer of particles 24.

Otherwise, a first inlet port to which liquid flows in and a first outlet port from which the liquid flows out are provided with the wall surface of the measuring vessel on the first chamber side. On the other hand, a second inlet port to which a liquid flows in and a second outlet port from which the liquid flows out are provided with the wall surface of the measuring vessel on the second chamber side. Here, the liquid is charged into the first inlet port to flow out from the first outlet port on the first chamber side and the other liquid is charged into the second inlet port to flow out from the second outlet port on the second chamber side. At that time, if the speed of flow in the second chamber is faster than that in the first chamber, the liquid flowing from the first chamber to the second chamber occurs through the pore 14. This liquid flow promotes the transfer to particles 24.

Furthermore, the liquid flow from the first chamber to the second chamber may be caused by electroosmotic flow. The liquid flow from the first chamber to the second chamber may be caused by a pressure difference between the first and second chambers. The electroosmotic flow and pressure difference may be generated by any publically-known means.

In the above example, the electric current measured is a signal detected when a constant voltage is applied; however, the signal detected therein is not limited to the electric current measuring in the constant voltage. The signal detected may be a voltage measured or a resistance when a constant current is applied. The current and resistance may be measured by any publically-known means. Here, the signal detected may be any one of electric characteristics generated during trans location of the target from the first chamber to the second chamber through the pore. Examples of electric characteristics include current, voltage and resistance and so on. And here, it is preferable that the signal detected is a pattern of the electric characteristic, for example, a wave pattern of it.

Furthermore, the power source 23 and ammeter 22 may not be provided with lead 20 on the electrode 17 side. That is, the ammeter 22 and power source 23 may be provided with lead 18 in this order from the first electrode 16 side.

In the above embodiment, the first electrode 16 and second electrode 17 are located on the wall surface of the measuring vessel. Note that the first electrode 16 and second electrode 17 have only to stay inside the first chamber and the second chamber, respectively. Thus, first electrode 16 may be disposed on the membrane contacting the solution in the first chamber and second electrode 17 may be disposed on the membrane contacting the solution in the second chamber or on the substrate 15. Or, the first electrode 16 may be connected to a first lead and disposed in the solution in the first chamber and second electrode 17 may be connected to a second lead and disposed in the solution in the second chamber.

Figure 3:
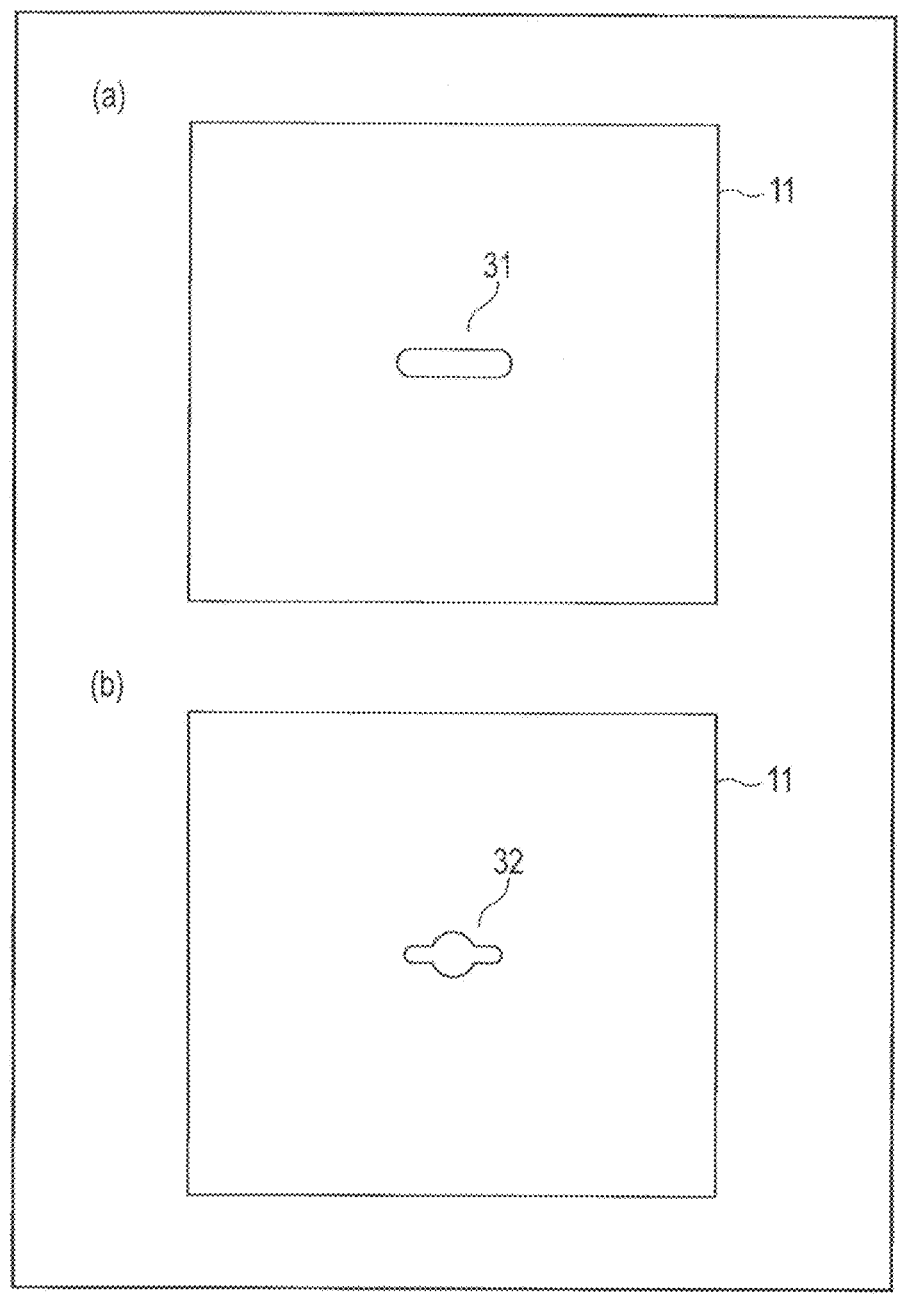
FIG. 3 is a plane view showing opening shape examples of a pore.

In the above embodiment, the pore 14 has a circular opening as shown in FIGS. 2(a) and 2(b). However, the shape of the opening part of the pore is not limited to being circular. As shown in FIG. 3(a), it may be an elongate hole 31. As shown in FIG. 3(b), it may be pore 32 having a combined circular shape in which a circle and an elongate hole overlap one another. The opening part may be of any other optional shape and may be changed to correspond to the shape of the target particle for the measurement. If a target particle has a disk-like shape or a rod-like shape, the opening part of the pore should be elongate hole as in FIG. 3(a) for better shape recognition. If a target particle has a Saturn-like shape or a spiked-spherical shape, the opening part of the pore should have the combined circular shape as in FIG. 3(b) for better shape recognition. Of course, the pore may be formed in any other shapes such as a rectangle, a polygon and combinations such as a combination of a rectangle and a polygon, and a combination of a rectangle or a polygon and an ellipse or a circle.

(3) Diameter of Pore and Thickness of Membrane

As described above, the electric current flows between first electrode 16 and second electrode 17 through the liquid in first chamber 12, pore 14, and the liquid in second chamber 13. The electric signal generated by the electric current is measured, and thereby, the size and shape of a target passing through the pore 14, in other words, the size and shape of particle 24 are measured. To achieve this measurement, the following relationship is important. When the diameter of the opening part of the pore 14 on the membrane 11 (hereinafter referred to as the diameter of the pore) is given d, and the thickness of the membrane 11 in the proximity to the pore 14 is given t, diameter d of the pore is greater than thickness t. Furthermore, when the diameter of spherical particles 24 to be measured is given a, diameter d of the pore 14 is greater than diameter a of the spherical particles 24. Thickness t of the membrane 11 in the proximity to pore 14 is smaller than diameter a of spherical particles 24. Hereinafter, the above relationship is described in further details.

FIG. 5 shows spherical particle 51 and rod-like particle 52 as examples of the targets. Here, diameter a is given for the spherical particle 51, and length L and width s are given for the rod-like particle 52. If the shape of the opening part is a circular shape as in FIG. 2(a), the diameter of pore 14 is d, and the thickness of membrane 11 in the proximity to the pore is t. Furthermore, as in FIG. 3(a), the opening part may be any shape such as elongate hole or a rod-like shape other than for a circular shape. In that case, the width of the elongate holr is referred to as diameter d for the pore. As in FIG. 3(b), the opening part may be shaped as a combination of an elongate hole and a circle. In that case, the smallest diameter of the opening part is referred to as diameter d. Under such conditions, diameter a of target particle 51, diameter d of pore 14, and thickness t of the membrane in the proximity to pore 14 satisfy $$t<a<d\leq 100a.$$

If the target is rod-like particle 52, width s, length L, diameter d of pore 14, and thickness t in proximity to pore 14 satisfy the followings:

$$s<d\leq 100s, \text{ and}$$

$$t<L.$$

Here, t and s can be t<s, or t>s, or t=s. L and d can be L<d, or L>d, or L=d.

A relationship between diameter a of the spherical particle 51 and thickness t of the membrane in the proximity to the pore 14 may satisfy: t to 100t<a, or more specifically, 2t<a, 5t<a, 10t <a, or 100t<a.

A relationship between diameter a of the spherical particle 51 and diameter d of the pore 14 may satisfy: 1 to 2<d/a≤5 to 100, or more specifically, 1<d/a≤75, 1<d/a≤50, 1<d/a≤25, 1<d/a≤10, or 1<d/a≤5.

A relationship between length L of the rod-like particle 52 and thickness t of the membrane in the proximity to the pore 14 may satisfy: t to 100t<L, or more specifically, 2t<L, 5t<L, 10t<L, or 100t<L.

A relationship between width s of the rod-like particle 52 and diameter d of the pore 14 may satisfy:

$$1 \text{ to } 2<d/s\leq 5 \text{ to } 100, \text{ or more specifically, } 1<d/s\leq 75,$$
$$1<d/s\leq 50, 1<d/s\leq 25, 1<d/s\leq 10, \text{ or } 1<d/s\leq 5.$$

Note that the proximity to the pore is a region in the membrane having thickness t which is required for the measurement of the size and shape of a target particle. If the diameter in the proximity to the pore is given A, the relationship between the region in the membrane having thickness t, A and diameter d of the pore may satisfy: 2d≤A≤15000t, or more specifically, 3d≤A≤10000t.

The measurement target may be a particle whose size is less than or equal to 1 mm. For example, the target is pollen, bacterium, and virus.

Pollen is a spherical particle whose diameter ranges from about 50 μm to about 100 μm. Examples of Pollen include, for example, cypress pollen (whose particle diameter ranges from about 30 μm to about 45 μm), cedar pollen (whose particle diameter ranges from about 30 µm to about 40 µm), and pine pollen (whose particle diameter ranges from about 45 µm to about 55 µm).

Examples of Bacterium include, for example, anthrax bacillus, pest bacillus, and botulinus bacillus. Anthrax bacillus may have the width ranging from about 1.0 µm to about 1.2 µm and the length ranging from about 5.0 µm to 2.0 µm. Pest bacillus may have the width ranging from about 1.5 µm to about 2.0 µm and the length ranging from about 1.5 µm to 2.0 µm. Botulinus bacillus may have the width ranging from about 0.5 µm to about 2.0 µm and the length ranging from about 2.0 µm to 10 µm.

Examples of virus include, for example, smallpox virus, bird flu virus, SARS virus, foot and mouth disease virus, and Ebola virus. Smallpox virus has the diameter of about 200 nm. Bird flu virus has the diameter of about 80 nm to about 130 nm. SARS virus has the diameter of about 60 nm to about 220 nm. Foot and mouth disease has the diameter of about 21 nm to 25 nm. Ebola virus is a string-like virus having the particle length of about 80 nm to about 800 nm.

To measure the above measurement targets, diameter d of pore 14 may be greater than 10 nm and less than 1 mm, or may be greater than 50 nm and less than 1 mm. For example, diameter d of pore 14 may be set greater than or equal to 10 nm, 30 nm, 50 nm, 75 nm, 100 nm, 150 nm, 200 nm, 500 nm, 800 nm, 1 µm, 2 µm, 3 µm, 5 µm, 10 µm, 20 µm, 50 µm, 75 µm, 100 µm, 250 µm, 500 µm, or 750 µm. Or, diameter d of pore 14 may be set less than or equal to 1 mm, 800 µm, 750 µm, 500 µm, 250 µm, 100 µm, 75 µm, 50 µm, 20 µm, 10 µm, 5 µm, 3 µm, 2 µm, 1 µm, 800 nm, 500 nm, 200 nm, 150 nm, 100 nm, 75 nm, or 50 nm. A range whose upper limit and lower limit are arbitrarily selected from the above will be preferable.

The thickness of the membrane 11 may be determined based on the size of the target, that is, the size of the diameter thereof. The thickness of the membrane 11 may be, for example, 10 nm to 500 nm or 20 nm to 450 nm. If the measurement target is bacterium for instance, the thickness of membrane 11 may preferably be 35 nm to 50 nm. However, the thickness of the membrane 11 is not limited to such ranges and can take any range as long as it satisfies the relationship between diameter a of the target, diameter d of the pore 14, and thickness t of the membrane in the proximity to the pore 14.

(4) Signal Detected When Two Differently Shaped Particles are Measured

The measurement method of (2) and the device described in (1) and (3) are used similarly in this example but the targets are two different particles.

Figure 6:
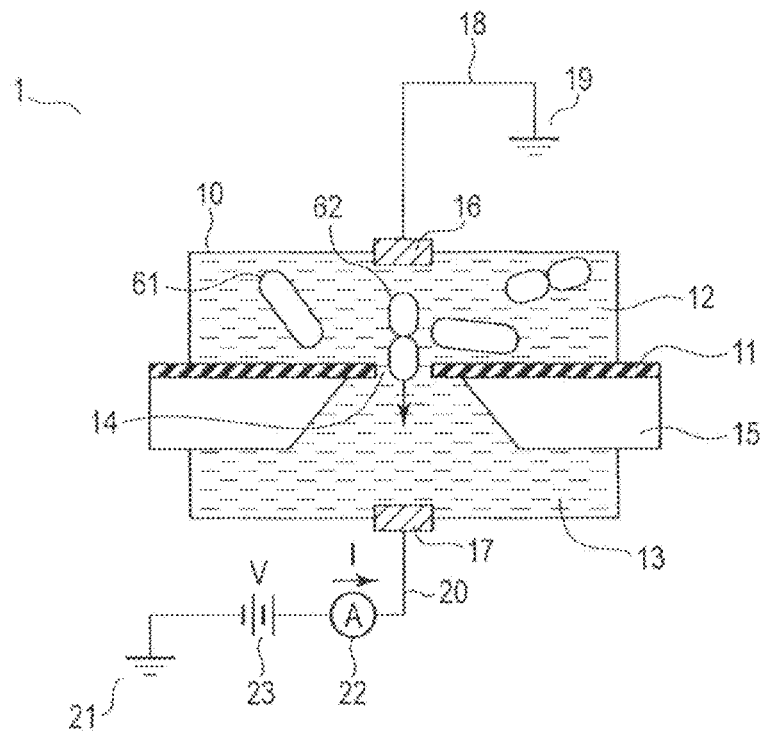
FIG. 6 is a schematic view showing a cross-sectional structure of the embodiments.

As shown in FIG. 6, the first chamber 12 contains two differently shaped particles, that is, particle 61 and particle 62. The particle 61 is a rod-like particle whose cross section taken along its longitudinal direction is a substantially constant circle. The particle 62 is a slender particle whose longitudinal axis is narrowed at its center. As in the above-mentioned method, voltage is applied between the first electrode 16 and the second electrode 17 by the power source 23. The electric current generated by this voltage supply is measured by the ammeter 22 over time or chronologically, for instance, it is measured for a predetermined time continuously or at a plurality of time-points in a predetermined time.

Figure 7:
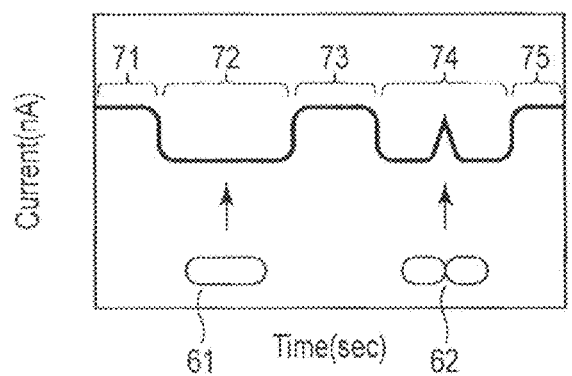
FIG. 7 is a graph showing an example of a signal detected in the embodiments.

FIG. 7 shows an example of changes in the electric current as a measured detection signal. If there is no particle in the pore 14, the electric current indicates a constant value (71). FIG. 7 shows how the electric current changes when the particle 61 and the particle 62 pass through the pore 14 in this order.

When the particle 61 exists in the pore 14, the electric current decreases depending on the size and shape of the particle 61 (72). After the particle 61 passes through the pore 14, the electric current returns to its original value (73). Then, the particle 62 passes through the pore 14, and the electric current decreases depending on the size and shape of the particle 62 (74). After the particle 62 passes through the pore 14, the current returns to its original value (75). While the particle 62 is passing through the pore 14, the electric current rises at the moment when the narrowed part at the center of its longitudinal axis comes in the pore 14, and here, how much the electric current rises depends on the shape of the narrowed part. Such chronological changes in the electric current can tell that the particles in the first chamber include the particle 61 and the particle 62, and that the particle 61 first passes through pore 14 and the particle 62 then passes through the pore 14. Through the above detection scheme, the size and shape of any particle in a specimen can be recognized by measuring chronological changes in the electric signal detected therein.

Figure 8:
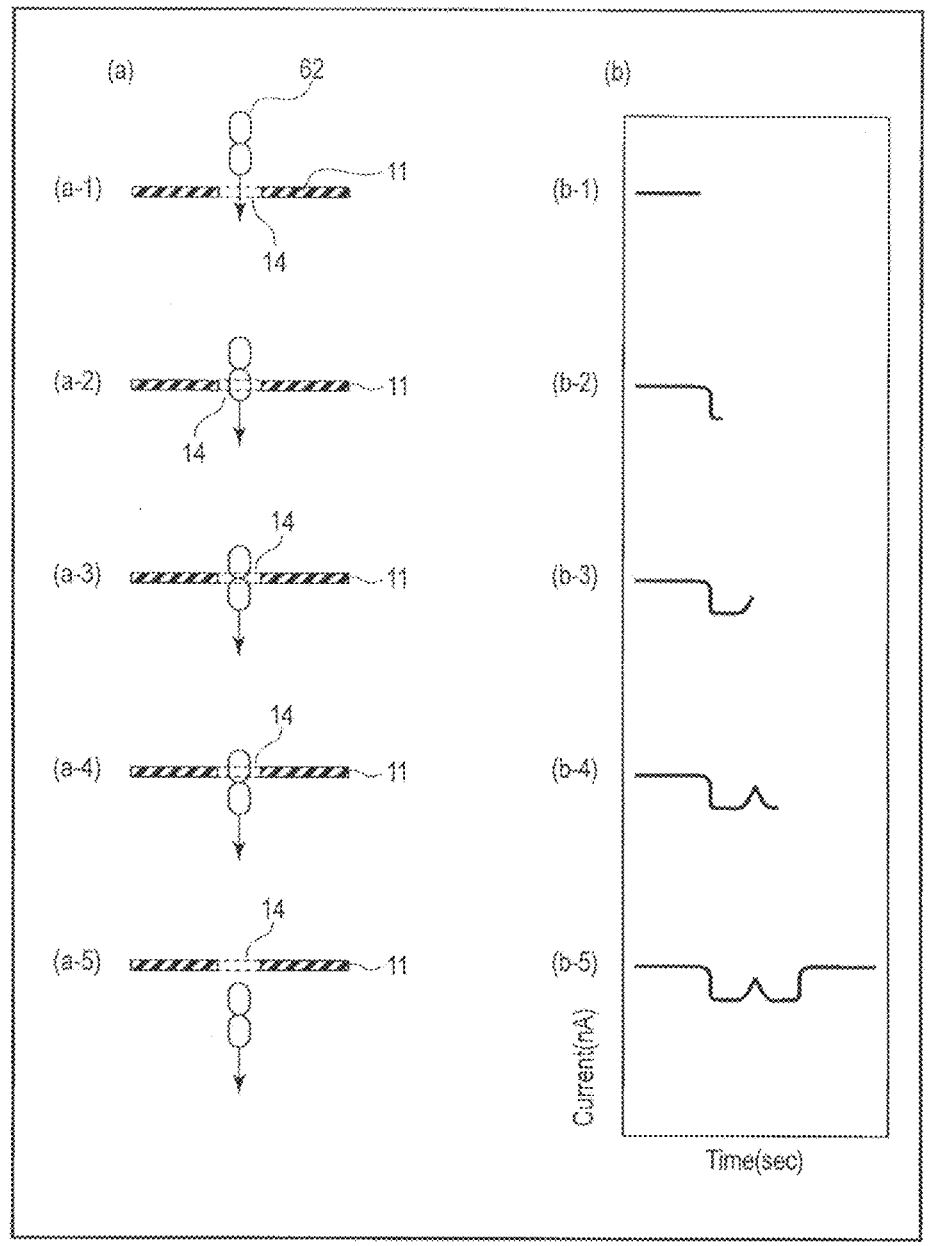
FIG. 8 is a graph showing transitional changes in the example of the signal detected in the embodiments.

Now, referring to FIG. 8, how the particle 62 passes through the pore 14 is explained chronologically together with a relationship with the electric signal. The series of FIG. 8(a) shows positional relationships between particle 62 and pore 14 changing as particle 62 passing through pore 14. The series of FIG. 8(b) shows chronological changes in the current being detected while particle 62 is passing through pore 14 corresponding to the particle position shown in the series of FIG. 8(a). Segments 8(a-1) to 8(a-5) show, from the top to the bottom, how particle 62 goes through the membrane in chronological order. The series of FIG. 8(b) includes segments 8(b-1) to 8(b-5). Segments 8(b-1) to 8(b-5) correspond to segments 8(a-1) to 8(a-5), respectively, and show, from the top to the bottom, how the electric current changes in chronological order.

Before the particle 62 enters the pore 14 (a-1), the electric current signal does not change from the base value (b-1). When particle 62 starts to enter pore 14 (a-2), the electric current falls depending on the shape of the part of the particle 62 passing through the pore 14 (b-2). Then, when the narrowed part of the longitudinal axis of the particle 62 reaches the pore 14 (a-3), the current rises (b-3). After the narrowed part of the particle 62 passes by the pore, the wider part reaches the pore 14 (a-4), and the electric current falls again (b-4). When the particle 62 completely passes by the pore 14 (a-5), the current returns to its original value (b-5).

By measuring the chronological changes in the electric signal detected in the above process, the size and shape of each particle in the specimen can be recognized. This phenomenon can be observed only when the thickness of the membrane 11 is set sufficiently thin as compared to the length of particle 62. Naturally, another embodiment can distinguish whether a target is one particle or an aggregation of two or more particles.

(5) Manufacturing Method of Membrane

Figure 9:
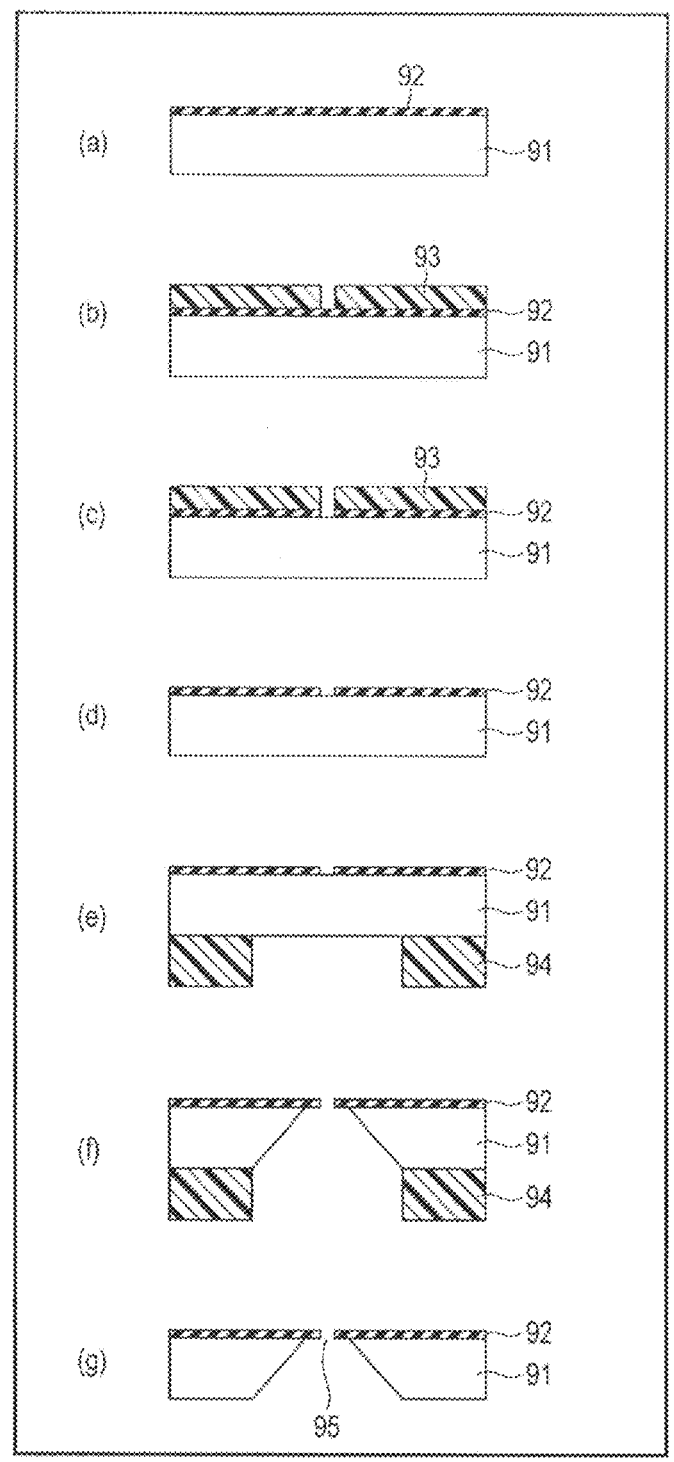
FIG. 9 is a schematic view showing an example of process for forming a pore in a membrane.

With reference to FIG. 9, an example of the manufacturing method of the membrane 11 is now explained.

In the first place, a $SiO_2$ film 92 is deposited on Si substrate 91 (FIG. 9a). The $SiO_2$ film 92 may be a thermal oxidation film, or a film formed with a thermal chemical vapor deposition (CVD) method or with a plasma CVD method. Then, resist 93 is coated on the $SiO_2$ film 92. An exposure and development process is performed to a region to be a pore in order to form an opening pattern in the resist

93 (FIG. 9*b*). The exposure may be performed by either a photolithography method or an electron beam lithography method. The photolithography method is used in general to form a pattern greater than 1 μm. The electron beam lithography method is used in general to form a pattern smaller than 1 μm. However, no limitation is intended thereby.

Then, the $SiO_2$ film 92 is etched using the formed pattern of the resist 93 as a mask (FIG. 9*c*). Etching may be performed as wet etching using $NH_4F$ or HF, or anisotropy dry etching such as reactive ion etching (RIE) using a $CF_4$ gas. Dry etching is preferable for greater pattern accuracy. Here, considering dry etching tolerance, the resist pattern may be transferred to a metal film, and then the $SiO_2$ film 92 may be etched using the metal film as a mask.

After the etching process, the resist is peeled off (FIG. 9*d*). Then, resist 94 is coated to the back surface of the Si substrate 91. Pattern forming is performed to open a region including a region to be a pore (FIG. 9*e*). The Si substrate 91 is etched using the pattern-formed resist as a mask in order to expose the part of the $SiO_2$ film 82 to be a pore (FIG. 9*f*). Lastly, the resist 94 used as the mask is removed (FIG. 9*g*). In etching of the back surface, the resist pattern may be transferred to a metal film before etching as mentioned in the above process.

Consequently, the membrane having the pore 95 which is defined by the film thickness of the $SiO_2$ film 92 is manufactured.

A film used for the membrane is not limited to a $SiO_2$ film, and may be any other insulating film such as SiN film or $Al_2O_3$ film. Furthermore, a material used for the substrate is not limited to Si, and may be glass, sapphire, ceramics, or resin.

For the back surface etching, any publically-known etching techniques can be used. Such techniques include, for example, perpendicular deep etching using $SF_6$ and $C_4F_8$ gasses, wet etching using KOH, and isotropy etching by $CF_4$ gas dry etching, but no limitation is intended thereby. The pore 95 is formed by forming a pore on a thin film on a substrate in the above, but no limitation is intended thereby. For example, a thin film with a pore formed preliminarily may be adhered to a supporting substrate to form a membrane having such a pore.

EXAMPLE 1

Manufacture of Membrane

An Si substrate of 10 mm square and 0.2 mm thickness was prepared. A TEOS film of 400 nm thickness was layered on the substrate as $SfO_2$ film. Then, a resist was coated thereon, and a circle pattern of 1.5 μm diameter to be a pore was formed on a first surface of the substrate by photolithographic exposure and development. The $SiO_2$ film was etched by a $CF_4$ gas. Perpendicular deep etching was performed on a second surface of the substrate by switching $SF_6$ and $C_4F_8$ gasses. Thereby, an area of 200 μm diameter was etched on the second surface. Then, the resist on the both surfaces on the substrate (that is, the first and second surfaces) was removed. Through these processes, a membrane having a pore which opens in a circle of 1.5 μm diameter was manufactured.

EXAMPLE 2

Manufacture of Membrane

An Si substrate of 10 mm square and 0.6 mm thickness was prepared and a SiN film of 20 nm was layered on the substrate. Then, a resist was applied thereon, and a circle pattern of 75 nm diameter to be a pore was formed by an electron beam lithography method. The SiN film was etched by a $CF_4$ gas using the resist pattern as a mask. Then, a resist was applied to the back surface and a resist pattern was formed by the photolithography. An opening part of 50 μm square was formed on the back surface by wet etching using KOH. The resist on the both surfaces was then removed. Through these processes, a membrane having a pore which opens in a circle of 75 nm diameter was manufactured. The membrane had the thickness of 20 nm in the proximity to the pore.

EXAMPLE 3

Single Particle Analyzing Device

Figure 11:
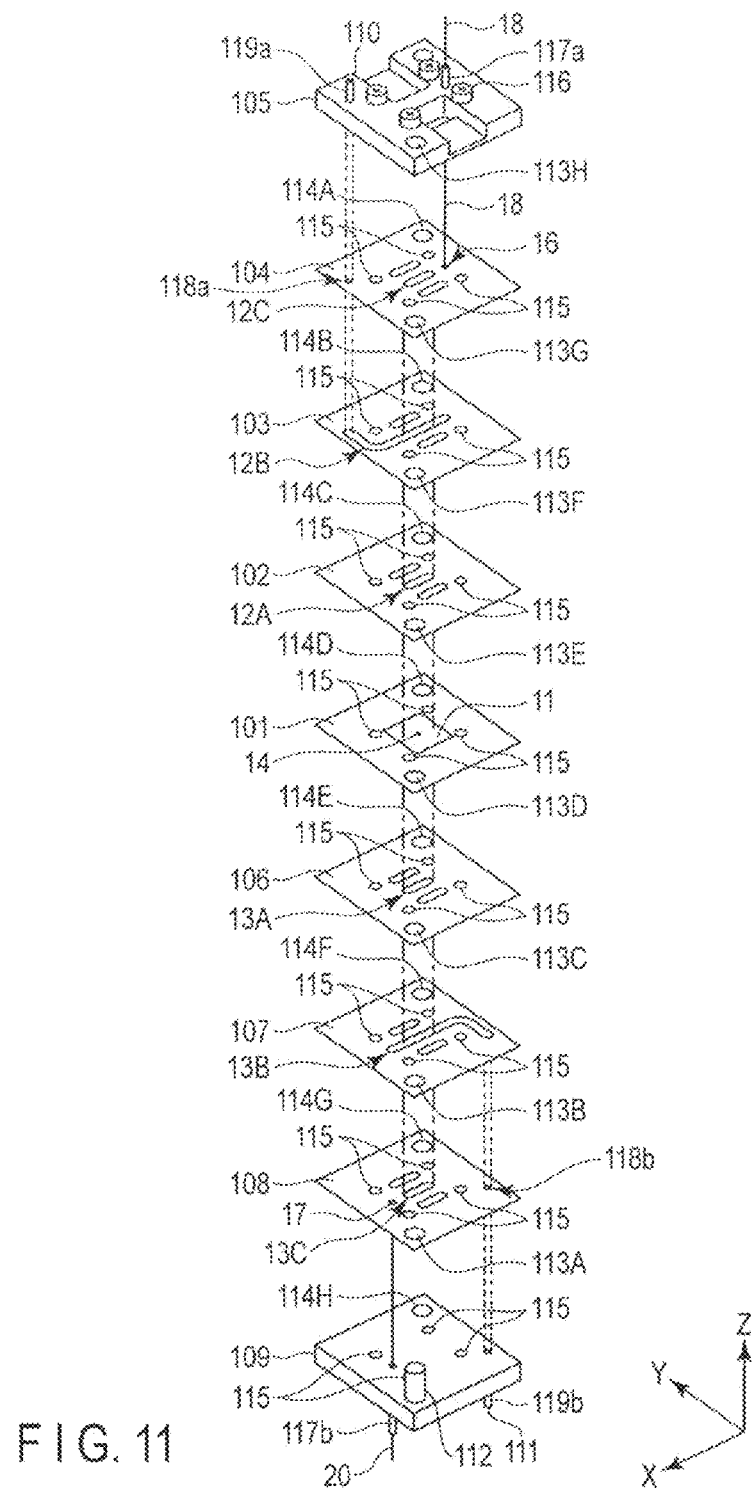
FIG. 11 shows an assembly diagram of a detection cassette.

A single particle analyzing device 1 was manufactured using the membrane of Example 1. The single particle analyzing device 1 is now explained with reference to FIGS. 10 and 11. FIG. 10(*a*) is a plane view showing the single particle analyzing device 1. FIG. 10(*b*) is a cross-sectional view showing the single particle analyzing device 1, taken along line B-B in FIG. 10(*a*). FIG. 11 shows the single particle analyzing device 1 in a assembly diagram. The single particle analyzing device 1 was manufactured in 10 mm square size and 0.5 mm thickness.

As shown in FIG. 11, the analyzing device is composed of nine layered plates fixed by screws 116. Firstly, the membrane of Example 1 with a pore opening therein was fixed at the center of a silicone rubber plate 101 having the thickness of 0.6 mm. Considering the thickness of the membrane, a recess of 10 mm square and 0.6 mm depth was preliminarily formed on the part to be fixed with the membrane. An opening part was formed at the center part of the silicone rubber plate 101 to expose the pore on the membrane and its proximity from the silicone rubber plate 101.

Upon the silicone rubber plate 101 up along Z-axis, first chamber 12 is formed. The first chamber here is composed of three plate-like members each having an opening part defining an inner space of the chamber and a cassette member. That is, the first chamber 12 is composed of a silicone rubber plate 102, acrylic plate 103, silicone rubber plate 104, and acrylic cassette member 105 stacked in this order upon silicone rubber plate 101 up along Z-axis (FIG. 10(*b*)). Each of the silicone rubber plate 102, acrylic plate 103, and silicone rubber plate 104 has the thickness of 0.5 mm.

On the silicone rubber plate 101 down along Z-axis, second chamber 13 is formed. The second chamber here is composed of three plate-like members each having an opening part defining an inner space of the chamber and a cassette member. That is, the second chamber 13 is composed of a silicone rubber plate 106, acrylic plate 107, silicone rubber plate 108, and acrylic cassette member 109 stacked in this order on silicone rubber plate 101 down along Z-axis (FIG. 10(*b*)). Each of the silicone rubber plate 106, acrylic plate 107, and silicone rubber plate 108 has the thickness of 0.5 mm.

Linear opening parts 12A, 12C, 13A, and 13C are provided with each of the silicone rubber plates 102, 104, 106, and 108 (FIG. 11). Each of the opening parts 12A, 12C, 13A, and 13C extends linearly along X-axis on the plane surface of each plate. Each of opening parts 12A, 12C, 13A, and 13C has the length of 7 mm and the width of 2 mm.

L-shaped opening parts 12B and 13B are provided with each of the acrylic plates 103 and 107. The opening part 12B extends linearly to one direction along X-axis and then bends to one direction along Y-axis on the plane surface of the acrylic plate 103. The opening part 13B extends linearly to the other direction along X-axis and then bends to the other direction along Y-axis. Each of the opening parts 12B and 13B has the length in X-axis of 20 mm, the length in Y-axis of 9 mm, and width of 2 mm.

The first chamber and second chamber defined as above have the volume of 40 μL.

A flow path to charge liquid into the first chamber is formed as a combination of an aperture 118a pierced on the silicone rubber plate 104, an aperture pierced on the cassette member 105, and a nozzle 119a having an opening part 110 connected to the apertures. A flow path to charge liquid into the second chamber is formed as a combination of an aperture 118b pierced on the silicone rubber plate 108, an aperture pierced on the cassette member 109, and a nozzle 119b having an opening part 111 connected to the apertures. When liquid is discharged from the first and second chambers, the liquid is discharged from these opening parts 117a and 117b. The nozzles 119a and 119b have the length of 10 mm and the internal diameter of 0.8 mm. Here, liquid charged in the first chamber does not necessarily pass through the nozzle 119a and may pass through the nozzle 117a instead. The liquid charged in the second chamber does not necessarily pass through nozzle 119b and may pass through the nozzle 117b. Or, the liquid may be supplied through an optional combination of the above routes.

Or, the liquid may be supplied to each chamber as follows. For the charge and/or discharge of the liquid to/from the first and second chambers, the liquid may be charged into the opening part 110 of the nozzle 119a and may be discharged from the nozzle 119b. Thereby, the liquid fills the first chamber and then, passes through the pore 14 to flow into and fill the second chamber. Or, this process can be reversed. That is, the liquid is charged into the opening part 111 of the nozzle 119b to fill the second chamber, and the liquid then passes through the pore 14 to flow into and fill the first chamber. In that case, for the charge and/or discharge of the liquid to/from the first and second chambers, the liquid is charged into the opening part 111 of the nozzle 119b and is discharged from the opening part 110 of the nozzle 119a.

As the first electrode 16, an Ag/AgCl electrode is located on the surface of the silicone rubber plate 104 to be exposed in the first chamber. As the second electrode 17, an Ag/AgCl electrode is disposed on the surface of the silicone rubber plate 108 to be exposed in the second chamber.

The above silicone rubber plates 101, 102, 104, 106, and 108, acrylic plates 103 and 107, and cassette members 105 and 109 were assembled with two positioning pins. A pin 112 was inserted into the pin holes 113A to 113H pierced on the plates. At the same time, the other pin which is not shown in FIG. 11 was inserted into the pin holes 114A to 114H pierced on the plates. With these pins, the plates were positioned suitably to be layered on one another. Then, four screws 116 were inserted into the holes 115 to secure the seven plates and cassette members 105 and 109.

An interconnect connected to the first electrode through the silicone rubber plate 104 and cassette member 105 projects to the outside of the single particle analyzing device 1 through the nozzle 117a, and was connected to the lead 18. An interconnect connected to the second electrode through the silicone rubber plate 108 and cassette member 109 projects to the outside of the single particle analyzing device 1 through the nozzle 117b, and was connected to the lead 20. Here, the electrodes were connected to the leads through the nozzles 117a and 117b as in the figure, but no limitation is intended thereby. For example (although this is not shown), holes may be pierced in the cassette members 105 and 109 on a straight line going over the pore 14 to pass electrodes therethrough right above and below the pore 14.

The voltage between the first electrode 16 and the second electrode 17 is applied through the lead 18 or lead 20. The leads 18 and 20 were connected to the earths, respectively (not shown). Furthermore, the ammeter and power source were provided with the lead 20 in this order (not shown).

EXAMPLE 4

Single Particle Analysis (1) Detection of Particle Having Diameter of 0.78 μm

Single particle analysis was performed using the single particle analyzing device 1 manufactured in Example 3.

The second chamber 13 was filled with a TE (10 m M Tris-HCl, 1 m M EDTA) buffer solution. The first chamber 12 was filled with a TE buffer solution with particles to be measured suspended therein. The particles to be measured were polystyrene microparticles having the diameter of 0.78 μm with carboxylate groups modifying their surfaces.

Figure 12:
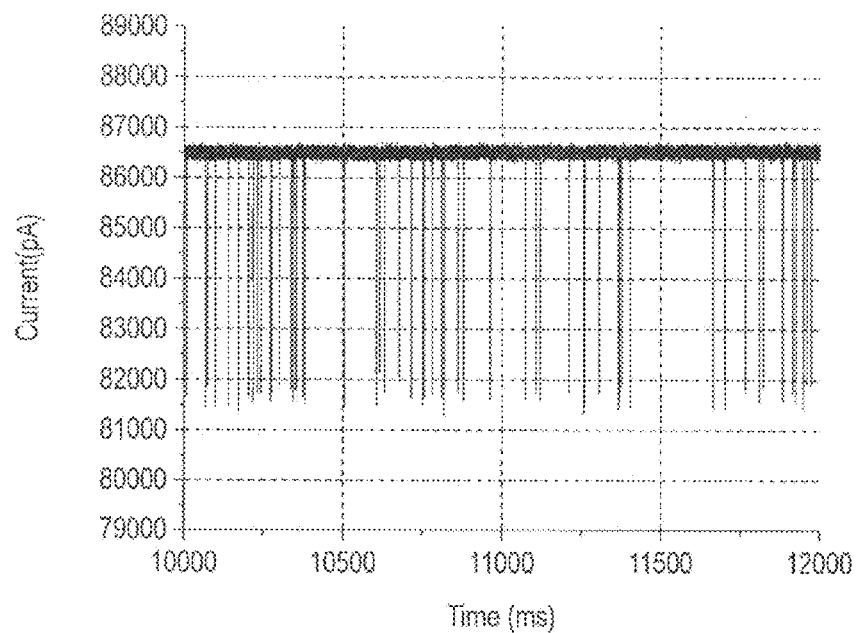
FIG. 12 is a graph showing a signal measured in examples.

Next, the first electrode was grounded and a voltage of 1 V was applied to the second electrode to measure the electric current. As a result of that, spiking current reductions of 4.9 nA were observed with respect to the base current of 87 nA as shown in FIG. 12. Each of lowering current signals spiking in the figure corresponds to a pore passage of a particle. Furthermore, when the bias is reversed, no signal is observed. From this point, it is understood that negatively charged particles are transferred to the direction of positive potential by the electrophoresis.

(2) Detection of Particle Having Diameter of 0.78 μm and Particle Having Diameter of 0.90 μm Using the single particle analyzing device 1 as structured in the above (1), the first chamber 12 was filled with a TE buffer solution with two kinds of particles having different diameters suspended therein. One is polystyrene particles having the diameter of 0.78 μm with carboxylate groups modifying their surfaces. The other is polystyrene particles having the diameter of 0.90 μm with carboxylate groups modifying their surfaces. The second chamber 13 was filled with a TE buffer solution.

Figure 13:
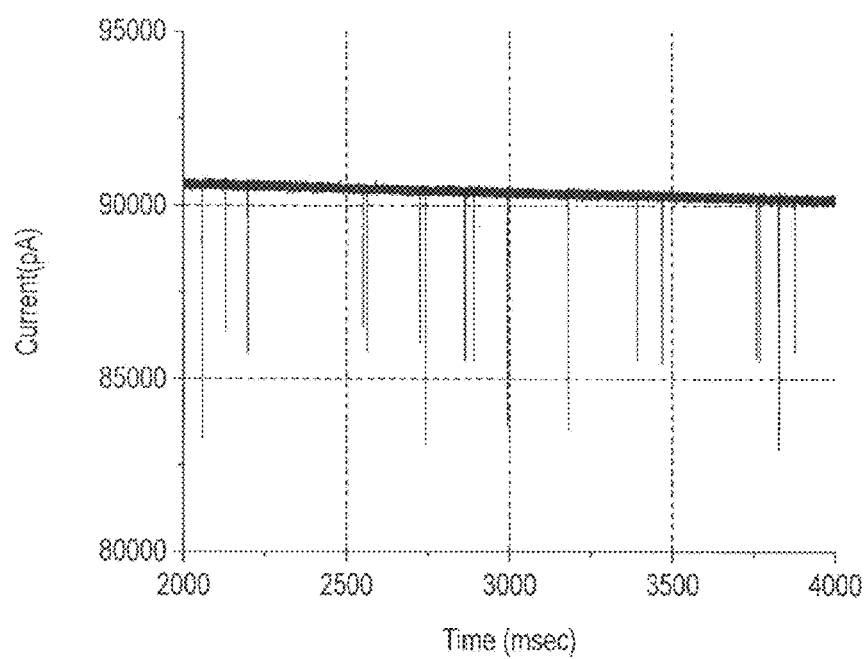
FIG. 13 is another graph showing a signal measured in examples.

A voltage of 1 V was applied to the second electrode 17 to measure the electric current. FIG. 13 shows the current signal measured therein. Lowering current signals spiking as in the signal detected in the above (1) were detected with respect to the base current of 90 nA.

Figure 14:
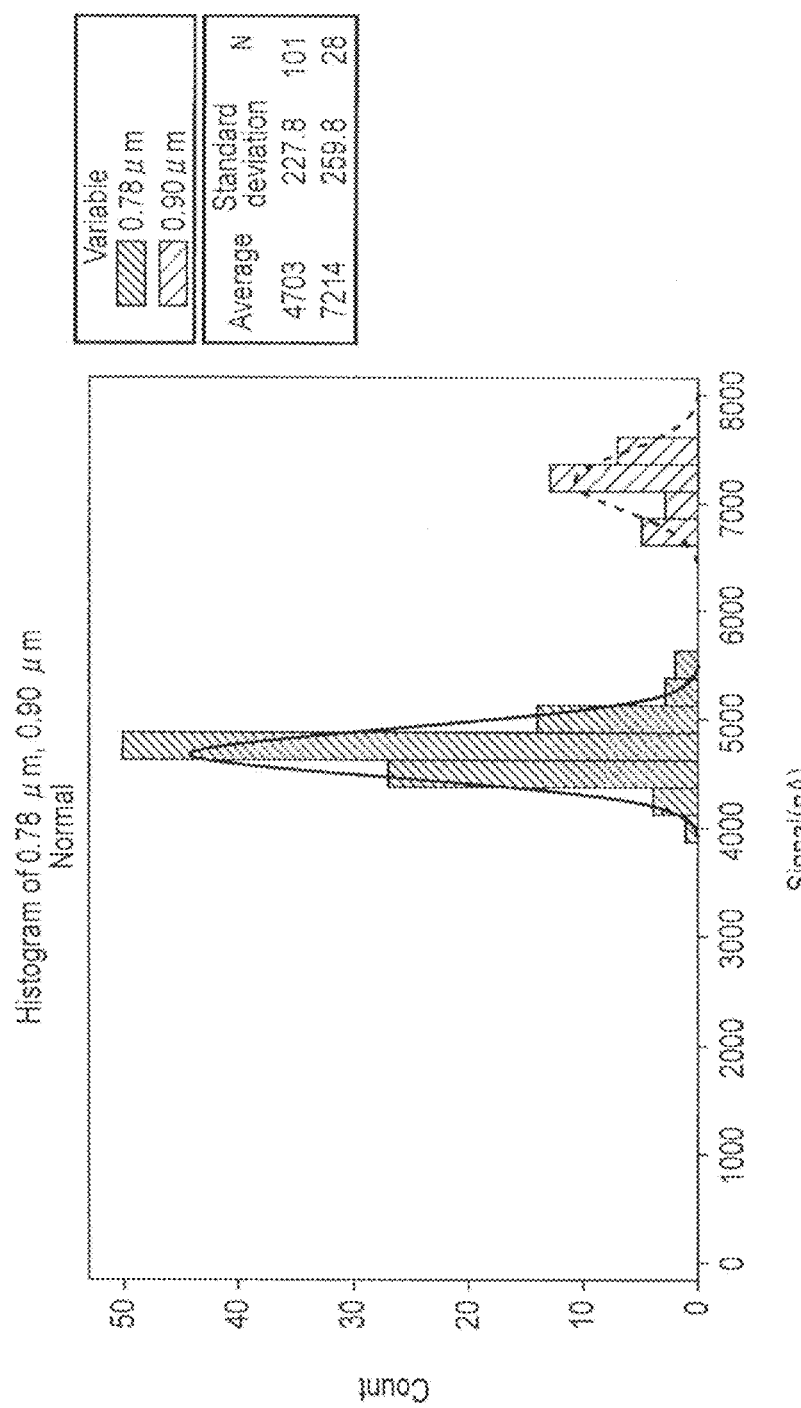
FIG. 14 is a histogram showing signal intensities of two particles having different diameters.

FIG. 14 is a histogram showing the intensity of reductions in the electric current from the base value. The histogram clearly shows the current signal intensity distributions at around 5 nA and at around 7 nA.

Here, the result from the above histogram was compared to the data obtained in the detection of a single particle having the diameter of 0.78 μm in the above (1) and the data obtained in the detection of a single particle having the diameter of 0.90 μm (which is not described above).

From this comparison, the distribution around 5 nA was identified as the signal from the particle of 0.78 μm diameter. Furthermore, the distribution around 7 nA was identified as the signal from the particle of 0.90 μm diameter. From the above, it was proved that a pore having the diameter of 1.5 μm in a membrane whose thickness around the pore is 430 nm can be used for identification of two kinds of the particles having the diameters of 0.78 μm and 0.90 μm, respectively, that is, two different particles having merely a 0.12 μm difference in size therebetween.

Such a single particle analyzing device can easily distinguish particles in various shapes such as bacteria, viruses, and pollens. When particles are analyzed by such a single particle analyzing device, particles in various shapes such as bacteria, viruses, and pollens can be identified easily.

EXAMPLE 5

Particle Shape Analysis

Based on the same method as in Example 2, a membrane formed of a SiN thin film having the thickness of 35 nm with a circular-shaped pore having the diameter of 1 μm was manufactured, and based on the same method as in Example 3, a single particle analyzing device with this membrane was manufactured. Using this analyzing device, particles having different shapes were measured. The second chamber 13 was filled with a TE (10 mM Tris-HCl, 1 mM EDTA) buffer solution. The first chamber 12 was filled with a TE buffer solution with the particles to be measured suspended therein. The particles to be measured here are polystyrene particles having the diameter of 0.78 μm with carboxylate groups modifying their surfaces. The polystyrene particles exist in the solution as monomers, dimers, and trimers. The monomer is a single particle existing alone. The dimer is a combination of two particles joined together partly at their surfaces. The trimer is a series of three particles joined together partly at their surfaces.

Then, the first electrode was grounded and a voltage of 100 mV was supplied to the second electrode to measure the electric current. FIGS. 15 to 18 show the results. The electric current reductions of approximately 400 pA were measured as spikes with respect to the base current of approximately 9.6 nA. FIG. 15(a) shows a signal measured at the time when a monomeric polystyrene particle passes the pore. The areas (1), (2), and (3) of FIG. 15(a) correspond to images (1), (2), and (3) of FIG. 15(b) showing relative position between the particle and the pore. When the monomeric particle passes the pore, the signal simply shows a single spike.

Then, FIG. 16(a) shows a signal measured at the time when a dimeric polystyrene particle passes the pore. This time, two consecutive lowering current spikes were measured. That is, the current signal draws two significant drops. FIG. 16(b) shows the shape of the particle calculated based on the measured current signal. Two spherical particles having the diameter of 0.78 μm are joined together partly at their surfaces therein. The narrowing joint part is considered to be 0.38 μm wide. FIG. 16(c) is a photo image of the measured dimeric polystyrene particle taken by a scanning electron microscope. From this photo image, it was proved that the shape calculated in FIG. 16(b) corresponded well to the polystyrene particle actually observed. FIG. 17(a) basically corresponds to FIG. 16(a) except that the base current is set 0 A. The areas (1), (2), and (3) of FIG. 17(a) correspond to images (1), (2), and (3) of FIG. 17(b) showing relative position between the particle and the pore. The area (2) of FIG. 17(a) corresponds to the electric current measured at the exact moment when the narrowing joint part is passing through the membrane.

FIG. 18(a) shows a signal measured during transfer of a trimeric polystyrene particle from the first chamber to the second chamber and passes the pore. This time, three consecutive lowering current spikes were measured. That is, the data draws three drops. The areas (1), (2), and (3) of FIG. 18(a) correspond to images (1), (2), and (3) of FIG. 18(b) showing relative positions between the particle and the pore. The current increase between the areas (1) and (2) in FIG. 18(a) corresponds to the time when the joint part between the first and second particles is passing through the membrane. The current increase between the areas (2) and (3) in FIG. 18(a) corresponds to the time when the joint part between the second and third particles is passing through the membrane.

Note that the calculation of the shape of the measurement target based on the change in the current is described in, for example, "Single-Nanoparticle Detection Using a Low-Aspect-Ratio Pore", ACS NANO, Vol. 6, No. 4, 3499 to 3505, 2012. The entire content of this document is hereby incorporated by reference herein.

As can be understood from the above, a shape of a particle can be identified from a shape of an electric current signal.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A single particle analyzing device comprising:
a measuring vessel;
a first chamber and a second chamber in the measuring vessel defined by an insulating membrane;
a pore opening in the membrane to connect the first chamber to the second chamber; and
a first electrode in the first chamber and a second electrode in the second chamber,
wherein the analyzing device is configured to measure a shape of a target by applying electric current between the first and second electrodes through the pore in the membrane and measuring a signal detected during translocation of the target from the first chamber to the second chamber through the pore, and
wherein the analyzing device satisfies the following dimensional relationships:

$t<d$ where d is a diameter of the pore, which is in a range of greater than or equal to 50 nm and less than or equal to 1 mm, the diameter d is greater than a diameter of the target, and t is a thickness of the membrane in the proximity to the pore, which is in a range of greater than or equal to 10 nm and less than or equal to 500 nm, the thickness t being less than the diameter of the target.

2. The single particle analyzing device according to claim 1, wherein the target is a particle having diameter which is in a range of greater than 10 nm and less than 1 mm.

3. The single particle analyzing device according to claim 1, wherein the target is selected from the group consisting of pollen, bacterium, and virus.

4. The single particle analyzing device according to claim 1, wherein the first and second electrodes are not in contact with the membrane.

5. The single particle analyzing device according to claim 1, wherein the membrane comprises a first surface and a second surface, the first surface being contacted with the first electrode in the first chamber, and the second surface being contacted with the second electrode in the second chamber.

6. A single particle analysis method, comprising:
(1) preparing a single particle analyzing device comprising a measuring vessel, a first chamber and a second chamber in the measuring vessel defined by an insulating membrane, a pore opening in the membrane to connect the first chamber to the second chamber, and a first electrode in the first chamber and a second electrode in the second chamber, and
wherein the analyzing device satisfies the following dimensional relationships:

$t<d$ where d is a diameter of the pore, which is in a range of greater than or equal to 50 nm and less than or equal to 1 mm, the diameter d is greater than a diameter of a target, and t is a thickness of the membrane in the proximity to the pore, which is in a range of greater than or equal to 10 nm and less than or equal to 500 nm, the thickness t being less than the diameter of the target,
(2) charging a conductive liquid into the first and second chambers;
(3) introducing targets into the first chamber; and
(4) measuring a shape of the target by applying electric current between the first and second electrodes through the pore in the membrane and measuring a signal detected during translocation of the target from the first chamber to the second chamber through the pore.

7. The single particle analysis method according to claim 6, wherein electricity is supplied between the first and second electrodes by applying a constant voltage, and the signal detected is an electric current.

8. The single particle analysis method according to claim 6, wherein the target is a particle having diameter which is in a range of greater than 10 nm and less than 1 mm.

9. The single particle analysis method according to claim 6, wherein the target is selected from the group consisting of pollen, bacterium, and virus.

10. The single particle analysis method according to claim 6, wherein the translocation of the target from the first chamber to the second chamber through the pore is promoted by electrophoresis of the target from the first chamber to the second chamber.

11. The single particle analysis method according to claim 6, wherein the translocation of the target from the first chamber to the second chamber through the pore is promoted by liquid flow from the first chamber to the second chamber.

12. The single particle analysis method according to claim 11, wherein the liquid flow is an electroosmotic flow.

13. The single particle analysis method according to claim 11, wherein the liquid flow is generated by a pressure difference between the first chamber and the second chamber.

14. The single particle analysis method according to claim 6, wherein the first and second electrodes are not in contact with the membrane.

15. The single particle analysis method according to claim 6, wherein the membrane has a first surface and a second surface, the first surface being contacted with the first electrode in the first chamber, and the second surface being contacted with the second electrode in the second chamber.

* * * * *

UNITED STATES PATENT AND TRADEMARK OFFICE
CERTIFICATE OF CORRECTION

PATENT NO.       : 9,726,636 B2  
APPLICATION NO.  : 14/484305  
DATED            : August 8, 2017  
INVENTOR(S)      : Sadato Hongo et al.

Page 1 of 1

It is certified that error appears in the above-identified patent and that said Letters Patent is hereby corrected as shown below:

On the Title Page

Item (30), the Foreign Application Priority Data has been omitted. Item (30) should read:  
--(30)    Foreign Application Priority Data  
Mar. 13, 2012    (WIPO)-----------PCT/JP2012/056372--

Signed and Sealed this  
Tenth Day of April, 2018

Andrei Iancu  
*Director of the United States Patent and Trademark Office*